United States Patent [19]
Peters

[11] Patent Number: 6,053,884
[45] Date of Patent: Apr. 25, 2000

[54] ANKLE BRACE WITH CUFF

[75] Inventor: Rick Peters, Fortville, Ind.

[73] Assignee: Athlete Protection Gear, LLC, Fortville, Ind.

[21] Appl. No.: 09/252,582

[22] Filed: Feb. 18, 1999

[51] Int. Cl.[7] .................................................. A61F 5/00
[52] U.S. Cl. ................................. 602/27; 602/5; 602/16; 602/23
[58] Field of Search ............................ 36/89, 115, 117.1, 36/117.5, 118.2; 602/5, 16, 20, 23, 24, 25, 26, 27, 28, 29, 65; D24/192; 128/877, 882; 482/79; 601/27, 33, 34; 623/47, 48

[56] References Cited

U.S. PATENT DOCUMENTS

| | | |
|---|---|---|
| Re. 33,395 | 10/1990 | Peters . |
| 76,353 | 4/1868 | Sherer . |
| D. 391,640 | 3/1998 | Oviedo, Jr. . |
| 1,205,206 | 11/1916 | Hofmeister . |
| 2,444,428 | 7/1948 | Carrier . |
| 2,973,757 | 3/1961 | Katthoefer . |
| 3,086,521 | 4/1963 | Desai et al. . |
| 4,280,489 | 7/1981 | Johnson, Jr. . |
| 4,517,968 | 5/1985 | Greene et al. . |
| 4,587,962 | 5/1986 | Greene et al. . |
| 4,665,904 | 5/1987 | Lerman . |
| 4,693,239 | 9/1987 | Clover, Jr. . |
| 4,834,078 | 5/1989 | Biedermann . |
| 5,031,607 | 7/1991 | Peters . |
| 5,056,509 | 10/1991 | Swearington . |
| 5,069,202 | 12/1991 | Prock . |
| 5,175,947 | 1/1993 | Parracho . |
| 5,177,884 | 1/1993 | Rullier . |
| 5,209,722 | 5/1993 | Miklaus et al. . |
| 5,678,330 | 10/1997 | Van Dyke et al. . |
| 5,778,563 | 7/1998 | Ahlbaumer . |

FOREIGN PATENT DOCUMENTS 562222  5/1957  Italy .

*Primary Examiner*—Kim M. Lee
*Attorney, Agent, or Firm*—Theresa Fritz Camoriano; Camoriano and Associates

[57] ABSTRACT

An ankle brace includes a heel stirrup including a base and left and right upright portions. Left and right pivot legs are pivotably connected to the left and right uprights, respectively. A cuff joins the left and right pivot legs. The left and right portions of the cuff preferably are pivotably connected to each other. The sides of the heel stirrup are tapered to provide maximum stability with minimum interference with the foot.

12 Claims, 6 Drawing Sheets

ANKLE BRACE WITH CUFF

BACKGROUND OF THE INVENTION

The present invention relates to ankle braces, and, in particular, to an ankle brace that provides greater comfort and support than braces of the prior art.

Many types of ankle braces are known, including my earlier design, described in U.S. Pat. No. Re. 33,395. That brace provided greater flexibility and comfort than other braces, because it provided pivots on both sides of the brace, which enabled the foot to flex forward and backward while limiting side-to-side motion of the foot relative to the leg in order to protect the injured ankle. That brace had left and right pivot legs, which were intended to lie along the left and right sides of the wearer's leg, and there were straps which wrapped around the leg to hold the pivot legs together. While the straps provide flexibility of movement, they also stretch and shift, thereby sacrificing some structural support.

Also, in prior art designs, the semi-rigid stirrup encircled the bottom of the foot, interfering with a person's foot spreading out as he put his weight on the foot, thereby causing irritation and pain. If the stirrup were made wide enough to avoid that problem, it would provide less support to the person's ankle and might be too wide to fit into the person's shoe.

SUMMARY OF THE INVENTION

The present invention provides the desired front-to-back flexibility of the prior art braces, and, in addition, provides improved structure so that there is additional structural support preventing side-to-side movement of the ankle.

In particular, the preferred embodiment of the present invention provides arms extending from the left and right pivot legs, and these arms are pivotably connected to each other. This pivot connection allows the brace to be adjusted in order to fit a wide variety of people's foot and leg shapes, resulting in a comfortable brace, while providing more support than prior art designs. The arms, pivoted together, limit the range of motion between the pivot legs while providing the desired flexibility so that the wearer can continue to flex and exercise the ankle while the ankle is protected and supported by the brace.

The present invention also provides a heel stirrup and a tongue, extending forward of the heel stirrup. The heel stirrup surrounds the heel to provide the greatest possible stability while leaving the bottom of the foot, including the arch, free to spread out, so that the stirrup does not impinge on the wearer's foot.

DESCRIPTION OF THE PREFERRED EMBODIMENTS

Figure 1:
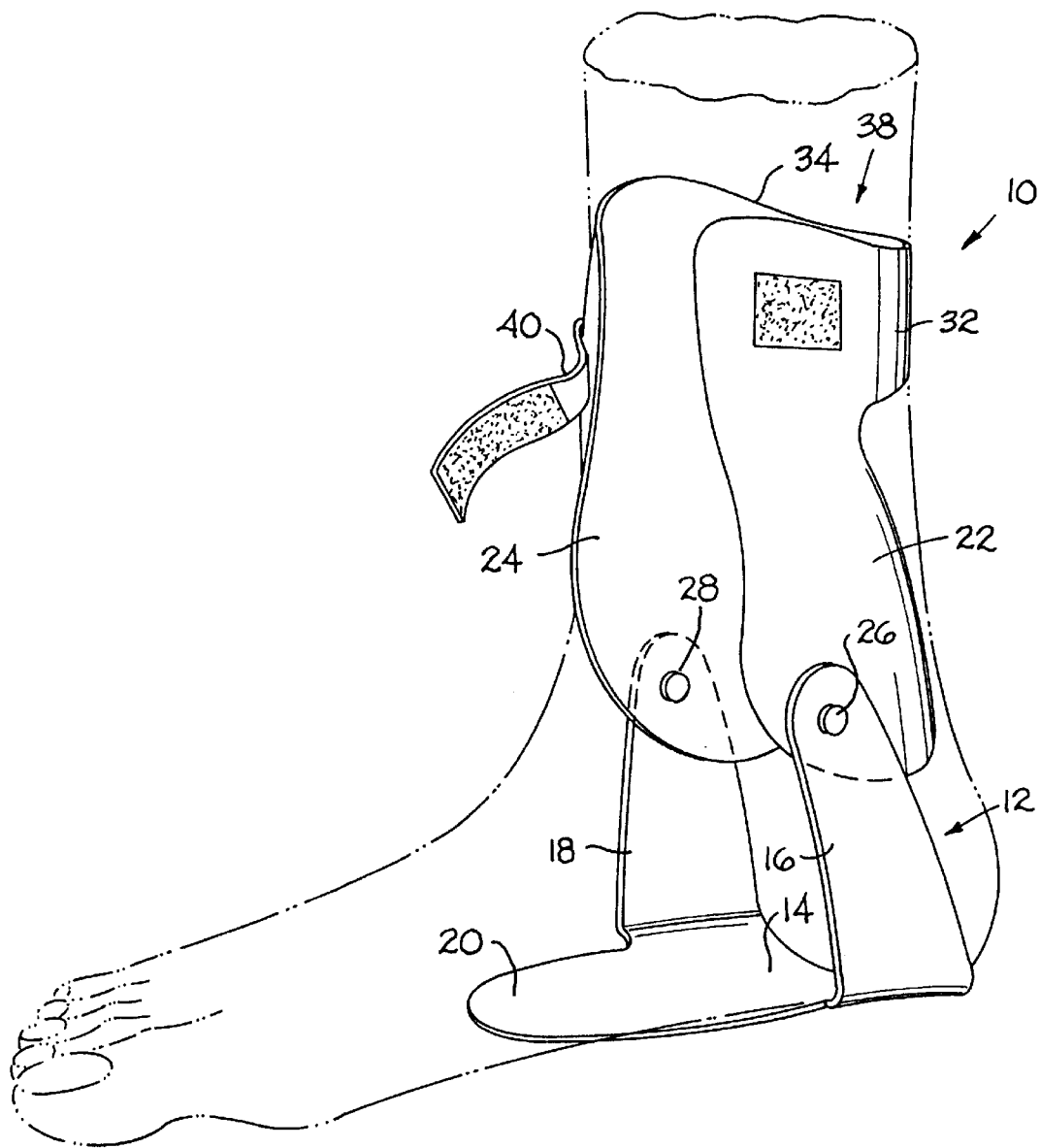
FIG. 1 is a perspective view of an ankle brace made in accordance with the present invention, with a wearer's foot shown in phantom.

FIGS. 1–5 show an ankle brace 10, which is made up of three main pieces. The first piece is the heel stirrup 12, which is substantially U-shaped, and includes a base or bottom portion 14 and left and right upright portions 16, 18. The upright portions 16, 18 project upwardly and forwardly from the rear of the base portion 14, which permits them to wrap around the heel, which provides for the greatest support, while still locating the pivots 26, 28 adjacent to the ankle, to provide the greatest comfort and flexibility. The horizontal distance "A" from the axis of the pivots 26, 28 to the rear of the stirrup 12 preferably is at least one inch. The horizontal distance "B" from the rear edge of the upright portion 16 at the height of the pivot 26 to the rear edge of the base 14 preferably is at least 0.75 inches and said left and right uprights extend at an angle from the rear edge. This location of the upright portions 16, 18 also prevents the stirrup 12 from interfering with the spreading of the foot. A tongue 20 extends forward from the forward edge 14A of the bottom portion 14 of the stirrup 12 to provide additional stability and support, again without interfering with the spreading of foot. The entire stirrup 12, including bottom portion 14, upright portions 16, 18, and tongue 20 are preferably molded or otherwise formed from a single or unitary piece of material. It would, of course, be possible to use separate pieces of material and connect them together to form the stirrup 12, but a single piece is preferable.

Figure 2:
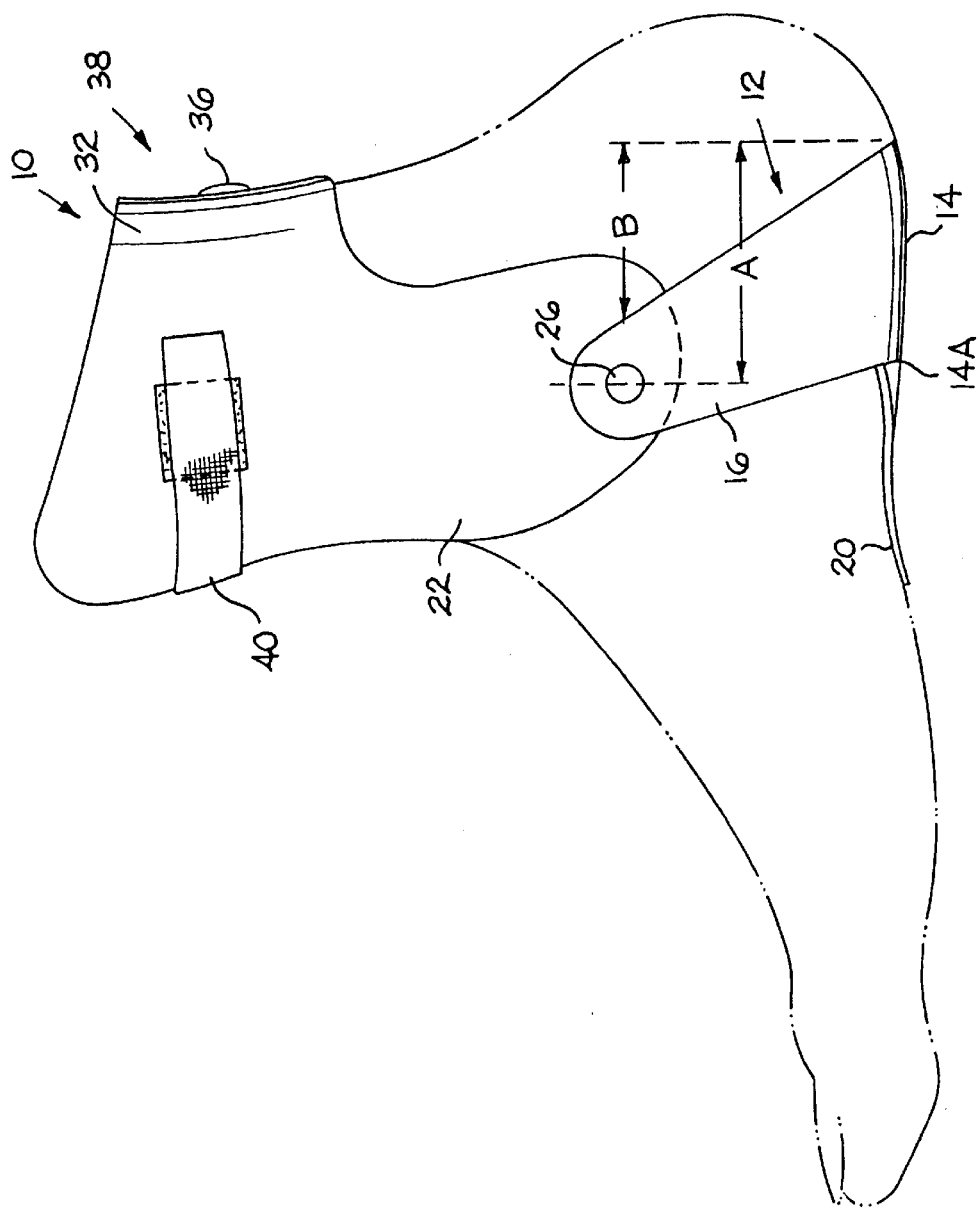
FIG. 2 is a side view of the ankle brace of FIG. 1.
Figure 3:
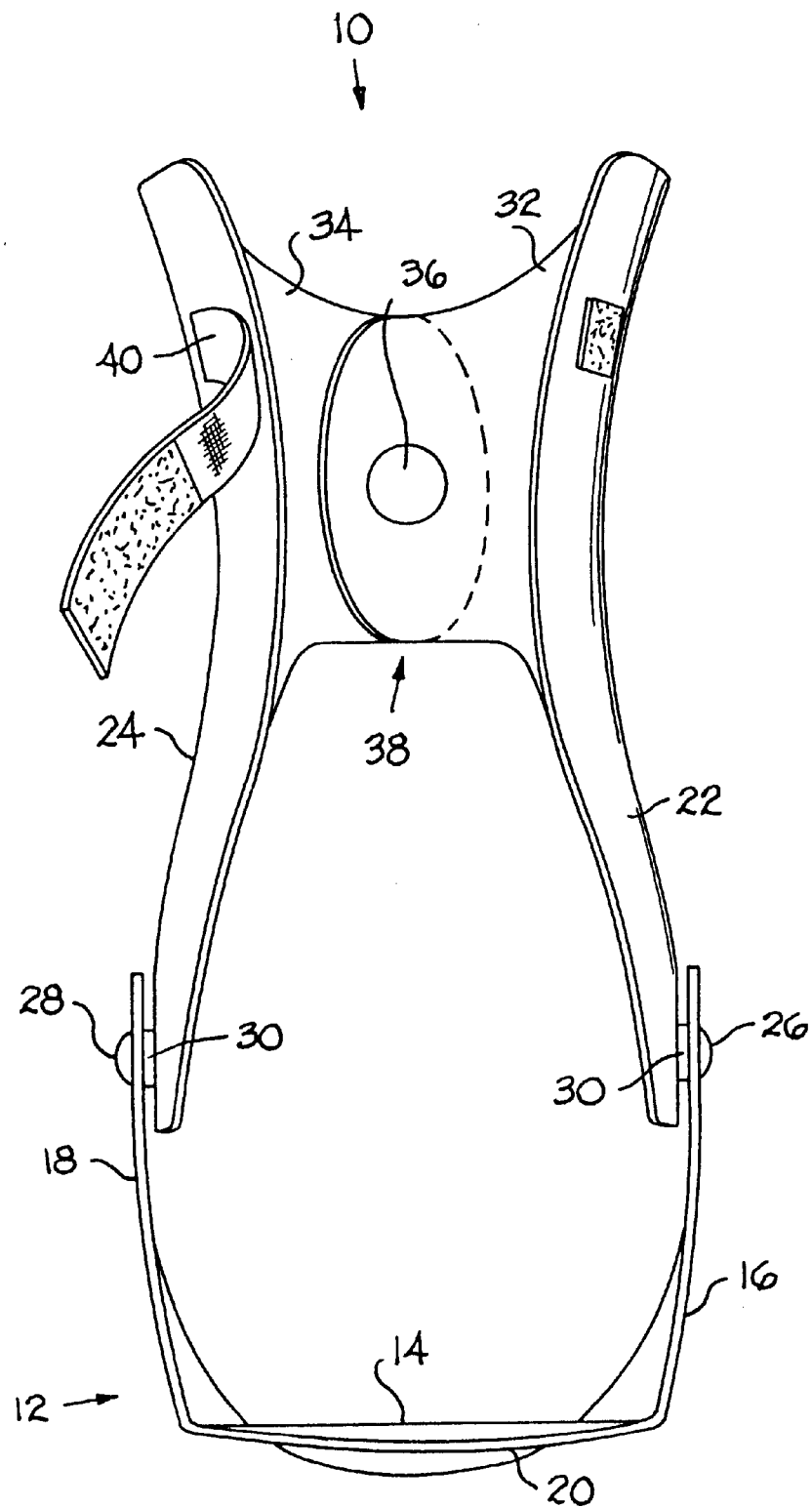
FIG. 3 is a front view of the ankle brace of FIG. 1.
Figure 4:
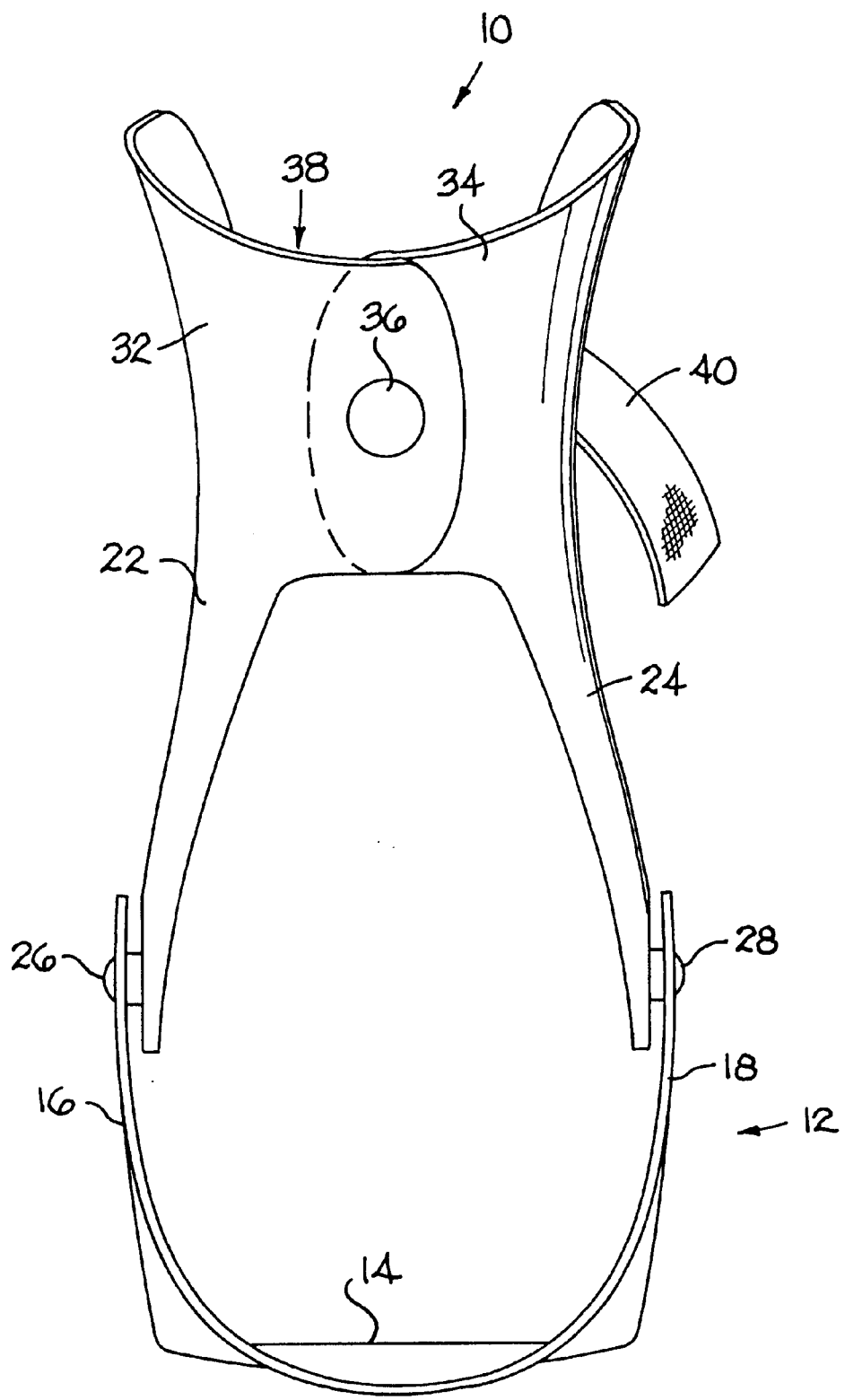
FIG. 4 is a rear view of the ankle brace of FIG. 1.
Figure 5:
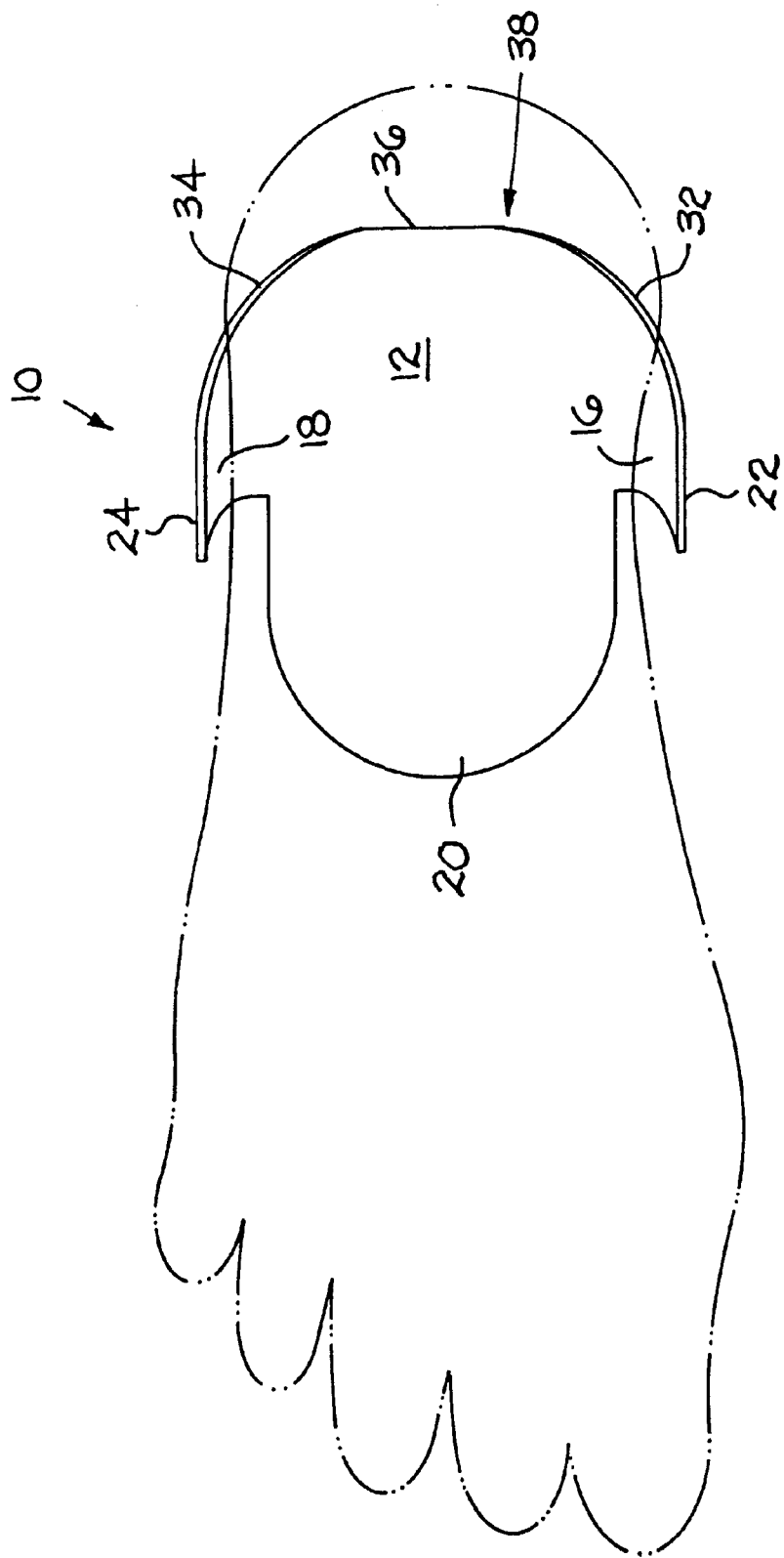
FIG. 5 is a top view of the ankle brace of FIG. 1.

The second and third pieces are the left and right pivot legs 22, 24, which are pivotably connected to the left and right uprights, 16,18, respectively, at the left and right pivot points 26, 28. The pivots 26, 28 are formed from bolts, rivets, or other connectors extending through the respective uprights and pivot legs, as shown best in FIG. 3 and are located approximately at the location of a wearer's ankle, so that the brace pivots forward and backward with the person's ankle. The two ankle pivot points 26, 28 preferably are at the same height. As shown in FIG. 2, the axis of the pivots 26, 28 is directly above the forward edge 14A of the bottom portion 14 of the stirrup 12. Also, as shown in FIG. 3, there preferably are spacers or washers 30 between the connected uprights and pivot legs to prevent them from rubbing against each other as they pivot.

The left and right pivot legs 22, 24 have rearwardly-projecting arms 32, 34, which overlap each other and are fastened together with a bolt, rivet, pin, or other connector to form a rear pivot point 36. The rear pivot point 36 is located along an imaginary vertical plane bisecting the brace 10, and its axis of rotation is substantially orthogonal to an imaginary vertical plane extending through the two ankle pivots 26, 28. A rear cuff 38 is formed by the two rearwardly-projecting arms 32, 34. The left pivot leg 22 and left arm 32 preferably are formed of a single or unitary piece of material, and, even if they are formed of separate pieces, it is preferred that the arm 32 be made of material at least as rigid as the leg 22 to which it is attached. This is also preferred with respect to the right pivot leg 24 and right arm 34.

A strap 40 is fastened at one end to the right pivot leg 24 and includes a strip of hook-and-loop fastener on its free end, and there is a mating piece of hook-and-loop fastener fixed to the left pivot leg 22, so that a wearer can put the brace on and then wrap the strap 40 around the front of his leg and fasten it to the left pivot leg 22 to hold the brace 10 on.

The brace 10 is shown here being used on the wearer's right foot, but the identical brace 10 could also be used on the left foot, as the brace is essentially symmetrical about a central vertical plane.

Figure 7:
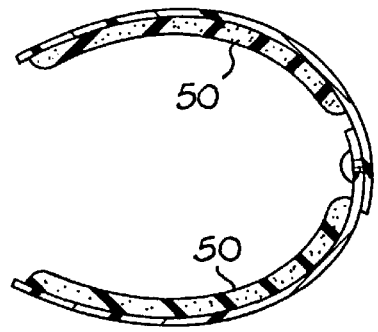
FIG. 7 is a view taken along the section 7—7 of FIG. 6.
Figure 6:
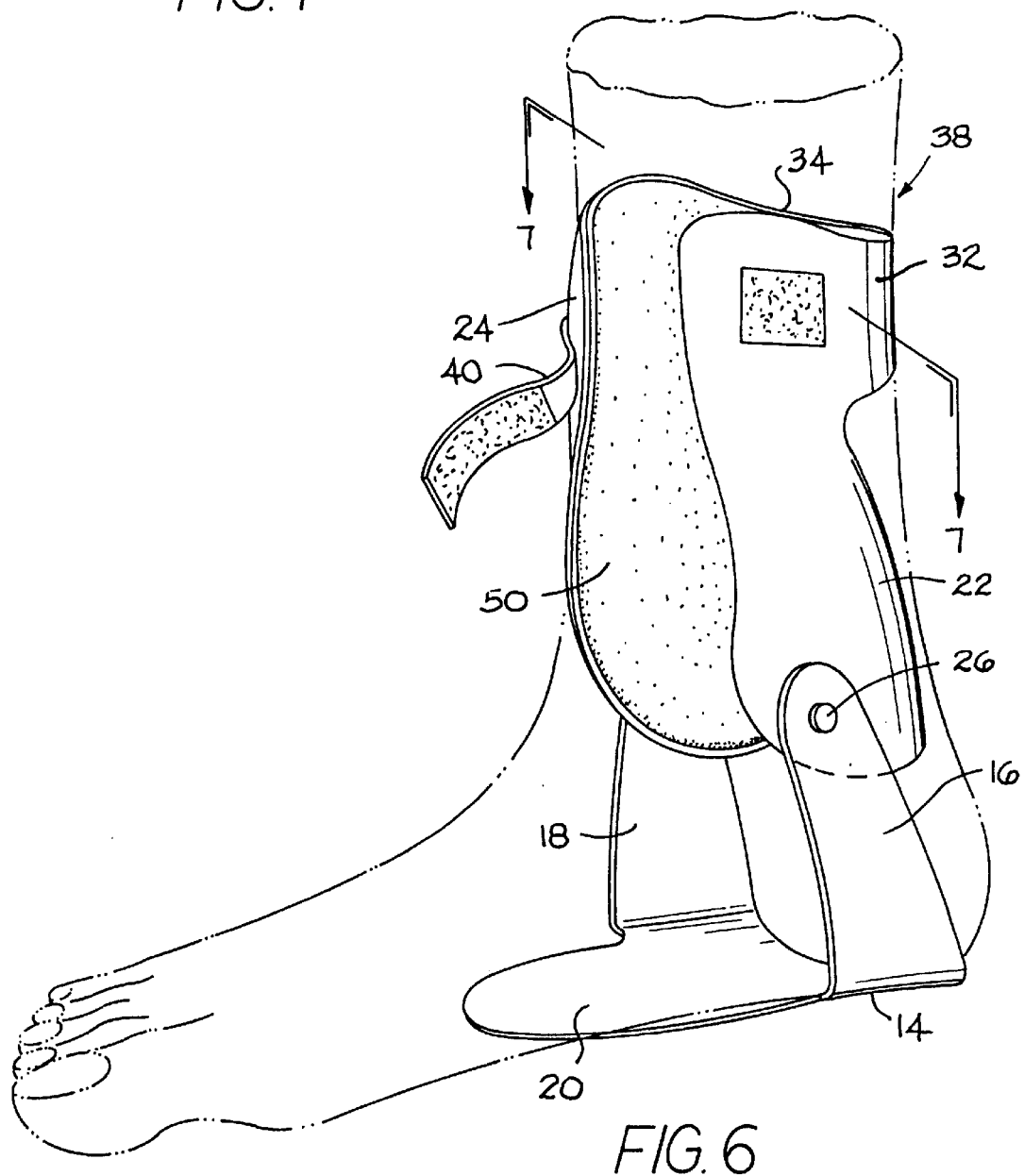
FIG. 6 is the same view as FIG. 1, but with padding added to the interior of the brace.

FIGS. 6 and 7 show the brace 10 of FIGS. 1–5 modified by the addition of padding 50 on the interior surface of the legs 22, 24 and arms 32, 34 of the brace. While these drawings show the use of foam padding, many different types of, pads, including air pillows, gel packs, and so forth, may be used.

It will be obvious to those skilled in the art that modifications may be made to the preferred embodiments described herein without departing from the scope of the present invention.

What is claimed is:

1. An ankle brace, comprising:
   a substantially U-shaped heel stirrup, including a bottom portion adapted to extend under the wearer's foot and left and right upright portions adapted to extend upwardly along the left and right sides of a wearer's foot during use;
   left and right pivot legs pivotably attached to said left and right upright portions at left and right pivot points, respectively;
   left and right arms projecting from said left and right pivot legs, respectively, wherein said left and right arms are pivotably connected to each other to form a rear cuff.

2. The ankle brace, as recited in claim 1, wherein the left and right arms project from said pivot legs in a rearward direction to form the rear cuff.

3. The ankle brace as recited in claim 2, and further comprising a strap fastened on at least one of said pivot legs adapted to wrap around the front of a wearer's leg.

4. The ankle brace as recited in claim 1, wherein the left arm and the left pivot leg are formed as a single piece, and the right arm and right pivot leg are formed as another single piece.

5. The ankle brace as recited in claim 1, wherein the left and right arms are at least as rigid as said left and right pivot legs.

6. The ankle brace as recited in claim 1, and further comprising a forwardly-projecting tongue extending from the bottom portion of the heel stirrup, so as to give stability to the brace without interfering with the spreading of the wearer's foot during use.

7. The ankle brace as recited in claim 6, wherein said heel portion defines a rear edge, said left and right pivot points are located at least one inch forward of said rear edge, and said left and right uprights extend at an angle from the rear edge to the pivot points to limit interference between the stirrup and the wear's foot while providing stability.

8. An ankle brace, comprising:
   a U-shaped heel stirrup, including a base and left and right uprights projecting upwardly from the base, wherein the base and uprights are formed as a unitary piece; and
   left and right pivot legs pivotably attached to said left and right uprights, respectively;
   each of said pivot legs including a unitary arm, extending rearwardly from an upper portion of said pivot leg, said unitary arms forming left and right cuff portions;
   wherein said left and right cuff portions are pivotably attached to each other.

9. The ankle brace as recited in claim 8, and further comprising a forwardly-projecting tongue extending from said base, and wherein said left and right uprights extend forwardly and upwardly from said base.

10. The ankle brace as recited in claim 9, and further comprising a strap, fastened to an upper portion of at least one of said pivot legs adapted to wrap around the front of a wearer's leg.

11. The ankle brace, comprising:
    a substantially U-shaped heel stirrup, including a bottom portion adapted to extend under a wearer's foot and left and right upright portions adapted to extend upwardly along the left and right sides of the wearer's foot;
    left and right pivot legs pivotably attached to said left and right upright portions at left and right pivot points, respectively;
    left and right arms projecting from said left and right pivot legs, respectively, wherein said left and right arms are joined together in a pivot connection to form a cuff;
    wherein said left and right uprights of said stirrup extend forwardly and upwardly from the rear of the base of said stirrup, so that the axis of the left and right pivot points is at least one inch forward of the rear of the base of said stirrup.

12. The ankle brace as recited in claim 11, and further comprising a tongue projecting forward from the base of said stirrup.

* * * * *

UNITED STATES PATENT AND TRADEMARK OFFICE
CERTIFICATE OF CORRECTION

PATENT NO. : 6,053,884
DATED : April 25, 2000
INVENTOR(S) : Rick Peters

It is certified that error appears in the above-indentified patent and that said Letters Patent is hereby corrected as shown below:

Claim 1, line 3 - delete "the", and insert - a -.

Claim 1, line 5 - delete "a", and insert - the -.

Claim 7, line 6 - delete "wear's", and insert - wearer's -,

Signed and Sealed this

Twentieth Day of March, 2001

Attest:

NICHOLAS P. GODICI

*Attesting Officer*    *Acting Director of the United States Patent and Trademark Office*